| (12) | United States Patent | (10) Patent No.: | US 7,032,263 B2 |
|---|---|---|---|
| | Falbo, Sr. et al. | (45) Date of Patent: | Apr. 25, 2006 |

(54) SONOGRAPHERS EXTENSION

(75) Inventors: Michael G. Falbo, Sr., Gladstone, MO (US); Martin Smoler, Shawnee Mission, KS (US)

(73) Assignee: Medical Positioning, Inc.

( * ) Notice: Subject to any disclaimer, the term of this patent is extended or adjusted under 35 U.S.C. 154(b) by 5 days.

(21) Appl. No.: 10/378,309

(22) Filed: Mar. 3, 2003

(65) Prior Publication Data

US 2004/0172755 A1  Sep. 9, 2004

(51) Int. Cl.
*A61C 7/00* (2006.01)

(52) U.S. Cl. .................... 5/600; 5/621; 5/658

(58) Field of Classification Search .......... 5/600, 5/621, 624, 503.1, 658, 630, 632–633; 297/140–143
See application file for complete search history.

(56) References Cited

U.S. PATENT DOCUMENTS

| 784,425 | A | * | 3/1905 | Phillips ................... 5/632 |
| 3,299,448 | A | * | 1/1967 | Rucchio ................... 5/633 |
| 3,565,419 | A | * | 2/1971 | Allard et al. ............. 5/634 |
| 5,184,363 | A | * | 2/1993 | Falbo, Sr. ................ 5/601 |
| D347,691 | S | | 6/1994 | Falbo, Sr. |
| 5,461,739 | A | | 10/1995 | Falbo, Sr. |
| 5,919,131 | A | | 7/1999 | Smoler et al. |
| 5,950,262 | A | | 9/1999 | Smoler et al. |
| 6,367,104 | B1 | | 4/2002 | Falbo, Sr. et al. |
| 6,557,196 | B1 | | 5/2003 | Falbo, Sr. et al. |

* cited by examiner

*Primary Examiner*—Suzanne Dino Barrett
*Assistant Examiner*—Fredrick Conley
(74) *Attorney, Agent, or Firm*—Shughart Thomson & Kilroy, PC

(57) ABSTRACT

A seat extension and/or a back support are provided for an examination table which allows a examiner to be seated fully on the examination table and in one embodiment to lean across the patient without the examiner having to contact the patient.

23 Claims, 3 Drawing Sheets

Fig. 9 though they may fall off the edge of the examination table,
SONOGRAPHERS EXTENSION

FIELD OF THE INVENTION

The present invention relates to the field of patient examination tables, more particularly, the invention comprises a seat extension and/or back support for an operator or sonographer positioned within an opening in an examination table used during echocardiography. The seat extension serving to expand the seating area of the examination table and being moveable or removable therefrom to permit movement of the examination table in a hospital or clinic environment and the back support providing the sonographer with a back bracing surface to provide support for the sonographer while examining or leaning across the patient.

BACKGROUND OF THE INVENTION

Figure 9:
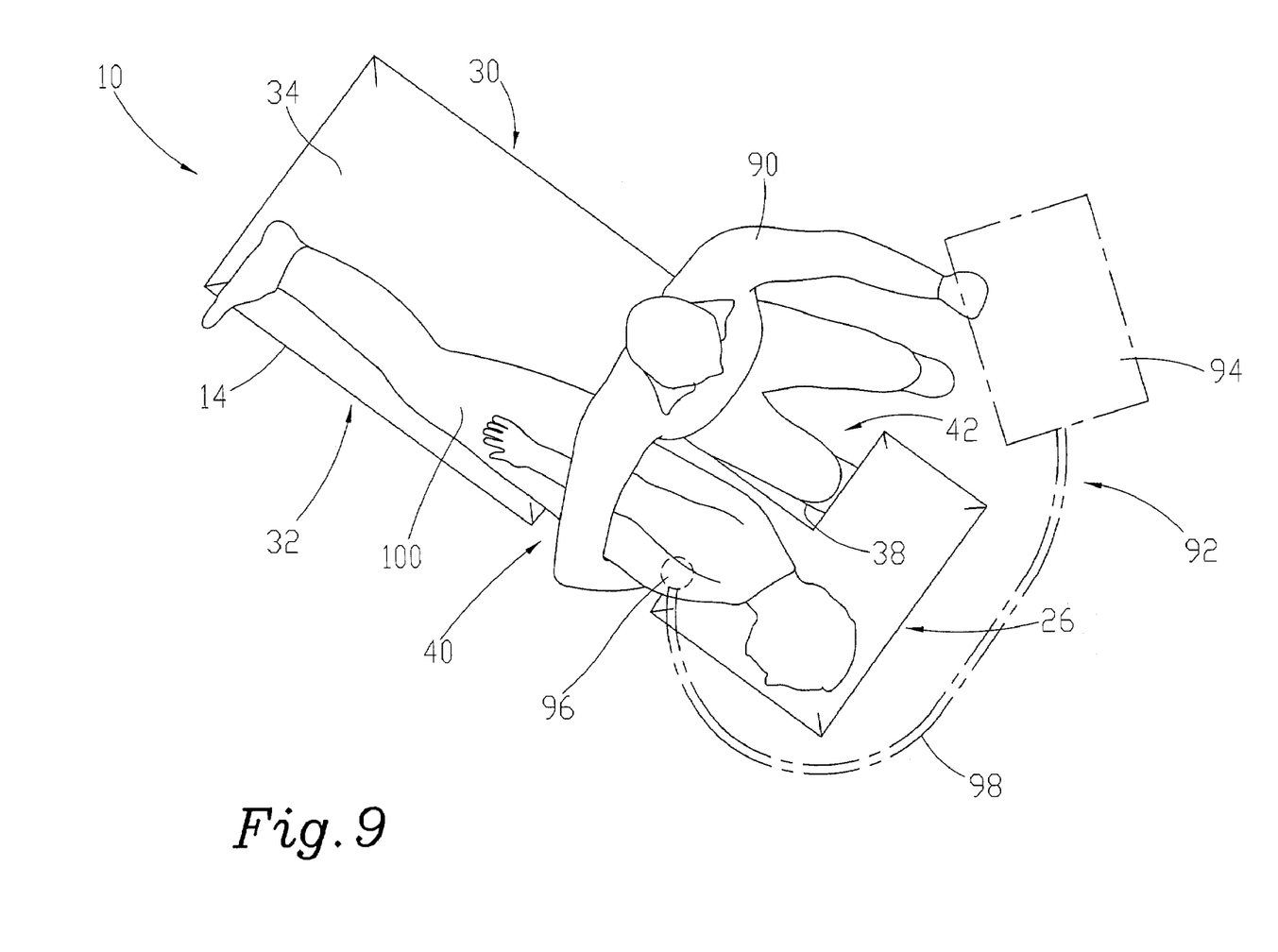
FIG. 9 is a plan view of a prior art examination table showing a sonographer positioned within an access site and a patient positioned on the examination table for an echocardiography procedure.

Patient examination tables such as those for echocardiography and in particular those tables shown in U.S. Pat. Nos. 5,919,131 and 5,184,363, and which patents are incorporated herein by reference, are provided with openings which allow the examiner to be positioned inboard of the edge of the table and next to a patient. This allows the examiner to reach over the patient's chest for application of an ultrasound examination probe to the patients chest wall next to the heart. As is shown in FIG. 9 the examiner can be seated on the deck 14 of the table 10 next to the patient 100. The examiner must reach across the patient to apply the probe 96.

This manner of conducting cardiac ultrasound or echocardiography examinations has a number of benefits over the prior art as it avoids the patient being situated on the edge of an examination table, it avoids the patient feeling as though they may fall off the edge of the examination table, it avoids the patient needing to support themselves on some other object during examination, and it provides full access to the patient's chest wall during examination. It should be appreciated that in prior art examination tables, that is examination tables lacking the inventive access sites as shown in U.S. Pat. No. 5,184,363 to Falbo, a sonographer cannot avoid the discomfort of being forced to stand, sit or straddle in unnatural or uncomfortable positions on or adjacent to the examination table. By use of the access sites examiners can avoid the need to reach across the entirety of a patient's body and the entirety of the examination bed to position the probe or diagnosis when dealing with obese patients.

While the examination tables having dual, adjacent, opposed access sites such as examination tables shown in U.S. Pat. Nos. 5,184,363 and 5,919,131 have eliminated many of the problems associated with prior ar tables, some discomfort, nevertheless, is still present for both examiner and patient when these examination tables are used in a particular fashion. For example, when a patient and examiner are positioned in the manner shown in FIG. 9, the positioning of the examiner and the patient can be uncomfortable depending on the sizes of the examiner and/or the patient. For example, if patient 100 is a large chested or stout person, it may be difficult for examiner 90 to reach around patient 100 to place probe 96 in proper contact against the patient's chest wall. In these situations, it is not uncommon for an examiner to lean over and across patient 100 thereby leaning on patient 100 and causing undesired contact between examiner 90 and patient 100 and/or causing examiner 90 to support some of his or her weight on patient 100. It further should be appreciated that during the procedure of echocardiography, it is not uncommon that the patient 100 will have just finished a portion of the examination procedure in which they raise their heart rate by pedaling a bicycle or walking on a treadmill. Having just exercised, the patient 100 can find the examiner's contact particularly uncomfortable. Therefore, it would be a benefit if a means were provided to maintain separation between examiner 90 and patient 100 when an echocardiography procedure as shown in FIG. 9 is being conducted.

Figures 1, 2, 3:
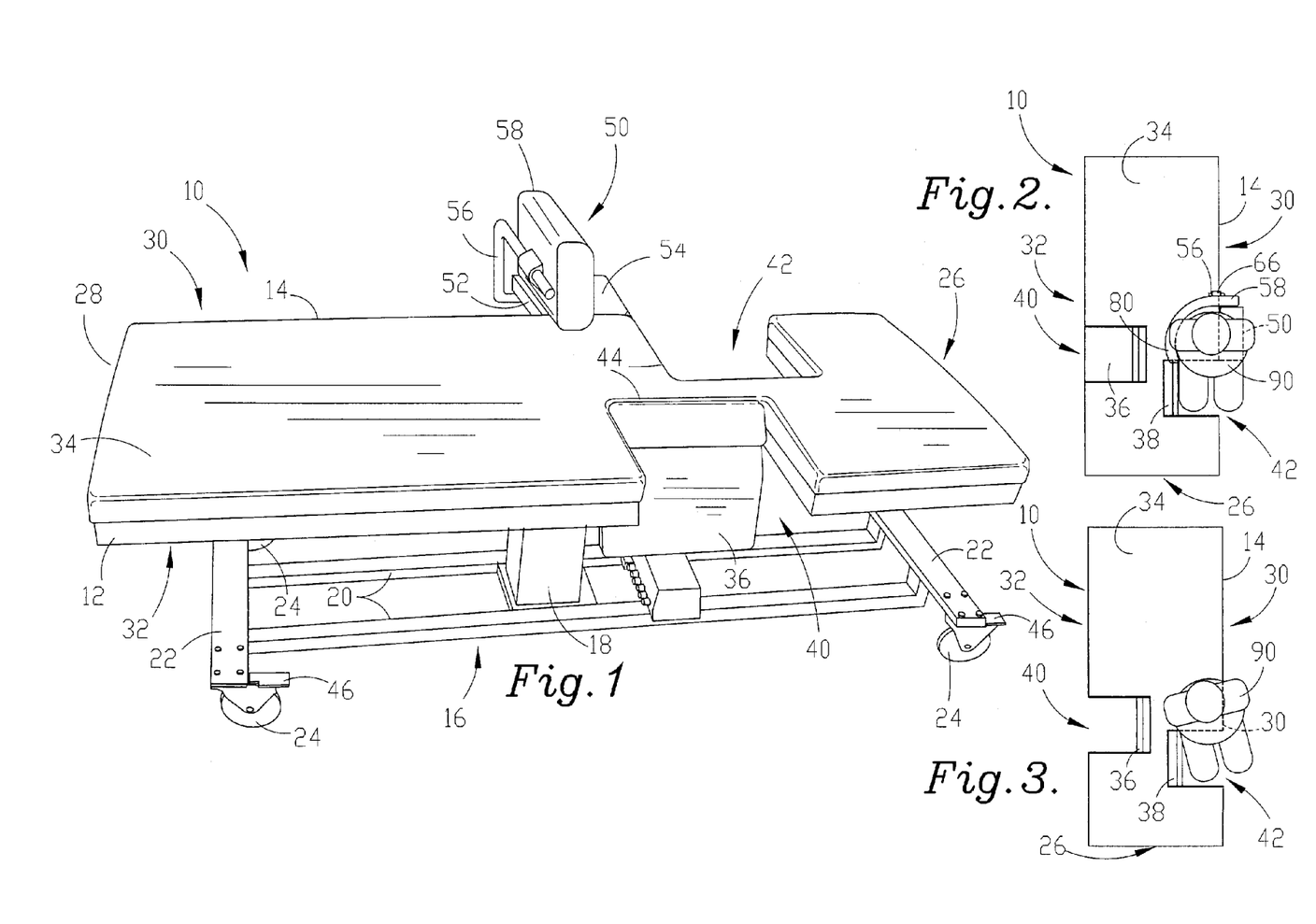
FIG. 1 is a perspective view of an examination table having one embodiment of the present invention attached to one side of the examination table.
FIG. 2 is a plan view of an examination table having an alternative embodiment of the present invention attached to the sonographer's side of the examination table (and showing a sonographer positioned thereon and with the patient's chest access site shown in the closed position) in the open position.
FIG. 3 is a plan view of a prior art examination table showing a sonographer precariously positioned thereon.

Additionally, it may be the case that an examiner 90 is a large or stout person. In this instance, it is not infrequent that the width of examination table 10 is insufficient to provide proper support to examiner 90 when examiner 90 is seated within access site 42. In such a situation, examiner 90 will be seated only partially on examination table 10 as is shown in FIG. 3. Alternatively, the examiner will feel the need to angle their body as shown in FIG. 3 to position more of her body on table 10. Such angled seating of examiner 90 on table 10 can present further difficulties to proper placement of probe 96 against the chest wall of patient 100. Also, if examiner 90 cannot fit fully within deck 14 of table 10, strain will be put on examiner 90's back, shoulder and/or arm which can lead to musculoskeletal injury or repetitive stress injuries of the back and hips of the sonographer 90.

It should be appreciated that it is not a practical solution to simply widen deck 14 of examination table 10. Frequently, examination tables must be moved around within a hospital or clinic. If deck 14 of table 10 were widened, it would not be possible to roll examination table 10 through many of the standard door openings presented in a hospital or clinic. Therefore, widening examination table 10 to better support examiner 90 is not a useful option. It will further be appreciated that access site 42 cannot be enlarged as expanding the size of access site 42 would reduce the amount of deck 14 available for the patient to lie upon. Moving the examiner nearer the patient by enlarging access site 42 would further exacerbate the problem of pushing the examiner 90 against patient 100 during examinations. It will also be appreciated that access sites 42 and 40 cannot be repositioned as this would move the examiner further away from the vicinity of the chest wall of patient 100 to which probe 96 must be applied. Therefore, it would be of great benefit to sonographers and the activity of echocardiography in general if a means were developed which would allow an examiner 90 to be fully seated upon deck 14 of examination table 10 to thereby avoid repetitive stress injury and/or musculoskeletal injuries which can result from the repetitive act of only being partially supported upon deck 14 of examination table 10 while conducting an examination.

It would be a further benefit if a means were provided to support the back of an examiner 90 while engaged in examinations to reduce the incidence of repetitive strain injuries due to the absence of any back support on an examination table 10 when an examiner is seated within access site 42 (FIG. 3).

It would be a further benefit if a means were provided to support the weight of an examiner 90 and/or to maintain the separation between an examiner 90 and a patient 100 (FIG. 9) when an examiner must reach across a large chested or stout patient to apply a probe 96 to the chest wall of the patient.

Such an invention would provide an examiner 90 with a proper upright seating position for conduct of echocardiography examinations, it would allow the examiner to be comfortable during such examinations avoiding bending and/or twisting to achieve the proper position. It would provide back support to an examiner and/or permit an examiner to support his or her weight on a portion of examination table 10 when it is necessary for an examiner to lean across a large chested or stout patient. Such an invention would benefit an echocardiography patient by maintaining separation between the examiner and the recently exercised patient and would prevent an examiner 90 from supporting his or her weight upon a patient during an examination procedure.

These benefits and more can be obtained through use of the present invention and without the need to widen examination table 10 or to extend access sites further into the center of deck 14 of table 10. In the method provided, a right handed sonographer scanning with the probe in their right hand and facing toward end 26, is able to sit on deck 14 of table 10 and to reach over a patient 100 (FIG. 9) while being fully supported by examination table 10 and without placing any of the examiner's weight upon the patient during examination.

SUMMARY OF THE INVENTION

The present invention solves these problems and limitations found in the prior art and provides a distinct advance in the state of the art. In particular, the apparatus and method of the present invention enable a sonographer to be seated fully on the deck of an examination table while the sonographer is positioned within an access site of the examination table while further permitting the examiner to have their back supported to assist in the prevention of repetitive stress injuries which can be caused by prior art examination tables. In another embodiment, the present invention provides for support and method of use which allow a sonographer to reach around a large chested or stout patient and apply a probe to the chest walls of the patient without excessively contacting the patient or the need to support any of the examiner's weight on the patient.

The present invention accomplishes these benefits and objects by providing a support which can be removed from the examination table deck and/or repositioned with respect to the examination deck and which provides additional space for support of the sonographer's body while seated in the access site of an examination table. In addition, the present invention provides a support which can support the back of the sonographer as well as support the body of a sonographer while seated in the access site. In one embodiment of the present invention, a support arm extends from the back support of the present invention to avoid the need to place weight on a patient as a sonographer leans across a patient to apply the probe to the patient's chest wall, the support arm also provides a method of supporting the weight of a sonographer when it is necessary for the sonographer to lean out across the patient to reach about the chest of a large chested or stout patient.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention.

DESCRIPTION OF THE DRAWINGS

Preferred embodiments of the invention, illustrative of the best modes in which the applicant has contemplated applying the principles, are set forth in the following description and are shown in the drawings and are particularly and distinctly pointed out and set forth in the appended claims.

DESCRIPTION OF THE PREFERRED EMBODIMENT

As required, detailed embodiments of the present inventions are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to FIG. 1 a typical prior art examination table 10 of the type described in U.S. Pat. No. 5,919,131 to Smoler et al. and U.S. Pat. No. 5,184,363 to Falbo is shown. Table 10 is comprised of frame 12 which supports table deck 14. The frame 12 and deck 14 are moveably supported by carriage unit 16. Carriage unit 16 is comprised of pedestal post 18 which supports frame 12 and deck 14 above carriage 16, pedestal 18 is mounted on rails 20 which are connected to cross members 22 having lockable wheels 24 attached thereto.

Deck 14 presents head 26, foot 28, side 30 and opposed side 32. Deck 14 further includes and supporting cushion 34. Deck 14 further comprises first, and second filler sections 36 (FIG. 1) and 38 (FIG. 2) which shift between closed and open positions in respective first, second access sites 40, 42. Deck 14 is preferably configured for supporting a patient on cushion 34 in the decubitus position as illustrated in FIG. 9. It will be appreciated that additional access sites can be provided in deck 14 as may be suitable to the particular application.

Each access site 40, 42 opens outwardly along a respective side 30, 32 of deck 14 and is preferably adjacent an inboard hinge wall 44. Each filler section 36, 38 is hingedly coupled with hinge wall 44 and configured as illustrated in U.S. Pat. No. 5,184,363 hereby incorporated by reference as part of the disclosure hereof. Each section 36, 38 is shiftable between an open position such as is illustrated for filler section 36 as shown in FIG. 1 and FIG. 2. When filler sections 36, 38 are in the open position (FIG. 3) they allow access therethrough, and when in the closed position (36 at FIG. 2) the filler section presents a contiguous support surface with cushion 34. Each filler section 36, 38 includes a conventional latch and release mechanism (not shown).

As shown in FIGS. 2 and 3, first access site 40 is located adjacent side 32, and second access site 42 is located adjacent side 30 of deck 14. More particularly, first access site 40 is located adjacent side 32 of deck 14 so that a patient's heart region is positioned above site 40 when the patient is positioned as shown in FIG. 9 with the patient's head adjacent head end 26. Second access site 42 is located for receiving a body portion such as the legs of a sitting examiner 90 or torso of a standing examiner conducting a medical examination as illustrated in FIG. 9.

Carriage unit 16 includes pedestal 18, rails 20, cross members 22, and wheels 24. The upper end of pedestal 18 is connected to table frame 12. Spaced, parallel, rails 20 are connected to the lower end of pedestal 18 on opposed sides thereof and extend substantially along the length of deck 14. Cross members 22 interconnect the ends of rails 20 as shown in FIG. 1. Wheels 24 are conventional and of the type commonly used with hospital gurneys and are coupled with cross members 22. Each wheel 24 includes a foot actuated brake lever 46. Wheels 24 enable carriage unit 16 to provide shiftable, that is, rolling support of deck 14 thereby allowing linear movement in any direction, but also rotational movement about an upright axis.

FIG. 9 shows one preferred environment of use for examination table 10 in order to perform a medical examination such as an echocardiogram. In performing an echocardiogram, an examiner or sonographer 90 uses an examination instrument 92 having base unit 94 and probe 96 coupled with base unit 94 by a flexible tether 98. As shown in FIG. 9, table 10 is oriented for use by examiner 90 holding probe 96 in the right hand for examining a patient 100. Patient 100 is positioned over access site 40 next to side 32 and the patient's head adjacent head end 26. The examiner could be a technician, physician or any other person qualified to use instrument 92.

In the orientation of FIG. 9, second filler section 38 (FIG. 2) is in the open position with the legs (or torso) of examiner 90 received in second access site 42. This allows examiner 90 to sit on deck 14 (or stand in site 42) to reach over and around patient 100 to position probe 96 through first access site 40 (with first filler section 36 in the open position) and into contact with the patient's heart region. As shown in FIG. 9, table 10 is also oriented and examiner 90 positioned so base unit 94 is in the range of view and within reach of the examiner's left arm for operation by the examiner. While the configuration of access sights 40, 42 have been demonstrated to be very useful and convenient for an examiner 90 conducting an examination of a patient's heart, and in particular providing ease of access to a patient's chest wall without the patient feeling as though they will fall off the edge of examination table 10 as in prior art examination tables, the difficulties as described in the background of the invention for an examiner 90 are well documented in medical literature and can result in substantial discomfort to an examiner who must continuously and on a daily basis examine patients while sitting on deck 14 of examination table 10. In particular, as previously described, it is necessary that deck 14 and frame 12 of examination table 10 be of a width that will pass through typical doors and other openings of a clinic or hospital or physicians office. Therefore the width of examination table 10 is limited.

As sufficient space must be provided on deck 14 for patient 100, it is frequently the case that an examiner must sit on deck 14 of examination table 10 with part of the examiners body off of deck 14. Referring now to FIG. 3 such a situation is shown for an examiner 90 who is in a seated position on deck 14 and within access site 42. As is shown in phantom lines in FIG. 3, side 30 of table 10 is positioned only partially under an examiner 90 sitting on deck 14 at access site 42. It will be appreciated from examination of FIG. 3 that the examiner's entry into access 42 is limited by the presence of filler section 38 which, while in the open position in FIG. 3, nevertheless provides some degree of obstruction to the full use of access site 42 by examiner 90. This results in examiner 90 being seated partially on deck 14 and partially off deck 14 as is shown in FIG. 3. Due to the necessary limitation on the width of examination table 10, it is not possible to simply provide a larger deck 14 and frame 12 to support examiner 90 on examination table 10. Were such a larger deck and frame provided, examination table would no longer be able to fit through doors and openings in a hospital or clinic as is necessary and desirable for use of examination table 10. As previously described, a further problem presented with prior art examination tables is that an examiner, when working in the position shown in FIG. 9, may need to lean across a patient 100 to properly position probe 96 against the chest wall adjacent the heart. This need to lean across patient 100 is particularly the case when patient 100 is large chested or stout and/or examiner 90 has short arms which do not easily reach across a patient 100. The present invention provides a solution to these problems by, in one embodiment providing an expanded portion of deck 14 and frame 12 adjacent an access site which supports the examiner while in a seated position within an access site. Also, the present invention, in one embodiment, provides a back support to ease the strain placed on an examiner who must examine patients throughout the day on a daily basis. In yet another embodiment of the present invention a combination back support and examiner support is provided which allows the examiner 90 lean out and over a larger stout patient while avoiding the need for the examiner to actually lean on the patient in order to reach the chest wall of the patient for application of probe 96 thereto. The structure and operation of the support of the present invention will now be described.

Figure 4:
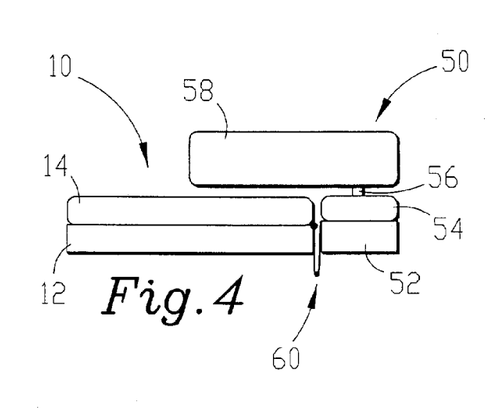
FIG. 4 is a front elevation view of the extension of the present invention and showing a hinge connection between the extension and the frame of the table to permit upward hinged movement of the extension to allow repositioning of the extension onto the cushion during movement or storage of the table and showing a detachable back support connected thereto.

Referring now to FIG. 4 examination table 10 is shown having the extension support 50 of the present invention attached thereto. Extension support 50 is generally comprised of an extension frame 52 supporting an extension cushion 54 a support post 56 extends from extension frame 52 to hold back support 58 in position above extension cushion 54 and deck 14 of examination table 10. Extension cushion 54 and extension frame 52 can be of any convenient size or shape, but generally dimensions of between 6 to 15 inches of additional width and 6 to 12 inches of additional seating depth adjacent to access site 40, 42 is sufficient to provide the additional needed support for an examiner 90 positioned in an access site 42 (FIGS. 2 and 3). It will be appreciated that extension frame 52 can be mounted to any structurally sound portion of examination table 10. This is accomplished by using a means for connection or a means for support such as hinge 60 or hinge 64 or other connectors or fasteners to connect extension frame 52 to frame 12 of examination table 10. The means for connection used for mounting extension support 50 and/or back 58 can include the use of hinged connectors, a slot or void in frame 12 for insertion of a connector therein, an externally mounted post or receiver on frame 12, or drawer-type slides which allow the extension to slide out from under frame 12. It will also be appreciated that in an alternate embodiment back support 58 can be mounted directly itself to frame 12 or to the resilient backing material of top 14 (not shown) where the extension cushion 54 may not be desired. Thus extension support 50 can be completely removable from examination table 10 or provided with a hinge or post or drawer glide or other means for connection to attach extension 50 to examination table 10. In the embodiment shown in FIG. 4 hinge 60 is a double hinge which permits extension 50 to swing upwardly and onto examination table deck 14 for movement of examination table through narrow doorways. It will be appreciated that when extension 50 is moved upwardly onto deck 14 that back support 58 maybe removed or rotated out of the way to allow extension cushion 54 and extension frame 52 to be placed on top of deck 14. To provide strength and support to the attachment of extension frame 52, examination table 10 hinge 60 can be a piano-type hinge which extends the length of extension frame 52 to provide secure attachment of extension frame 52 to frame 12 of examination table 10. To lock extension 50 into position with respect to examination table 10 a catch or lock 62 (FIG. 6) is provided to prevent hinged movement of extension 50 when such movement is not desired. Post 56 supports back support 58 of extension 50. Post 56 can be fixed with respect to extension frame 52 or can be vertically extendable and horizontally repositionable depending upon the particular construction employed. Those skilled in the art will appreciate the varieties of construction which can be used in the attachment of back support 58 to extension frame 52 or extension cushion 54.

Figure 5:
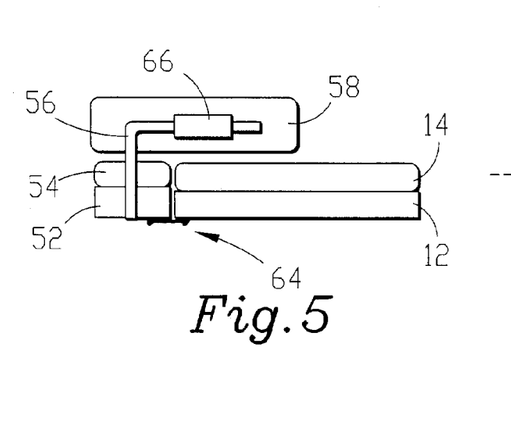
FIG. 5 is a rear elevation view of the extension of the present invention and showing a hinge connection between the extension and the frame of the table to permit downward hinged movement of the extension to allow repositioning of the extension under the frame of the table during movement.

Referring now to FIG. 5 the rear view of the embodiment of FIG. 4 is shown. However, rather than upwardly moving hinge 60 a downwardly swinging hinge 64 is shown. In the embodiment shown in FIG. 5 extension frame 52, extension cushion 54, post 56 and back support 58 are structurally similar to the embodiment shown in FIG. 4. In the embodiment of FIG. 5, downwardly swinging hinge 64 is provided to show the option of allowing extension 50 to swing underneath examination table 10 if it is needed to move examination table 10 from one location to another within a clinic or hospital. Again, in the embodiment of FIG. 5 catch 62 (FIG. 6) has been deleted for clarity. It will be appreciated that back support 58 extends well into the area of deck 14 of table 10 thereby to be available to support the back of an examiner 90 who is in a seated position within access site 42 (FIG. 2). Back support 58 is attached to post 56 by rotatable connector 66 which allows back support 58 to pivot on post 56 as shown by Arrow P in FIGS. 6 and 8.

Instead of using a hinge as the means for connection between table frame 12 and extension 50 other means for connection can be substituted. For example the use of a hinged attachment can be eliminated in favor of the use of insertion posts which extend from extension frame 52 and insert into voids in table frame 12 or a connection bracket can be attached to examination table 10 and a flange or post connection inserted into the bracket or flange. In this embodiment the voids would be positioned near access site 40, 42 and would provide flush alignment with cushion 34 of deck 14 and with the access site opening.

Figure 6:
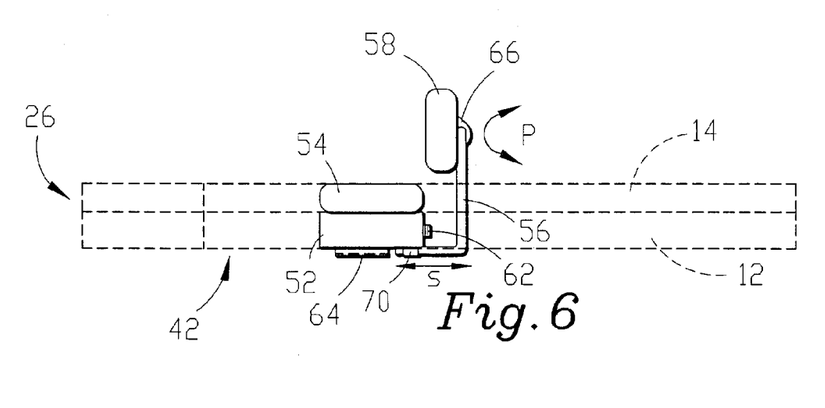
FIG. 6 is a side elevation view of the extension of the present invention and showing the table frame and deck in phantom lines.

Referring now to FIG. 6 the embodiment of extension 50 shown in FIGS. 4 and 5, but showing only hinge 64 is presented. Extension 50 is shown mounted on examination table 10 such that the front edges of frame 52 and cushion 54 align with the edge of access site 42 that is farthest away from head end 26 of table 10. It will be appreciated that as uniform surfaces are intended to be provided between cushion 54 of extension 50 and cushion 34 of deck 14 of table 10 that cushion 54 will generally be positioned so it is flush mounted with cushion 34 of deck 14. As previously discussed catch 62 is mounted on frame 12 of table 10 to retain extension 50 in a position for supportive use when hinge 64 is not being employed to swing extension 50 out of the way for movement of table 10 throughout a clinic or hospital. As shown in FIG. 6 post 56 is retained and supported by frame 52 through the insertion of post 56 into post holder 70 mounted on the underneath side of frame 52. Post holder 70 is of the type which it allows slidable entry of post 56 into holder 70 to allow adjustment of the position of back support 58 either closer to cushion 54 or farther away from cushion 54 by sliding post 56 into and out of post holder 70 in the directions indicated by Arrow S.

Figure 7:
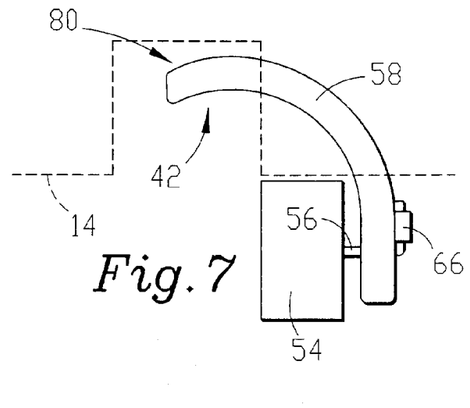
FIG. 7 is a plan view of an alternate embodiment of the present invention showing a curved back support to allow the sonographer to lean across, for example, a larger patient without the need to contact the patient.
Figure 8:
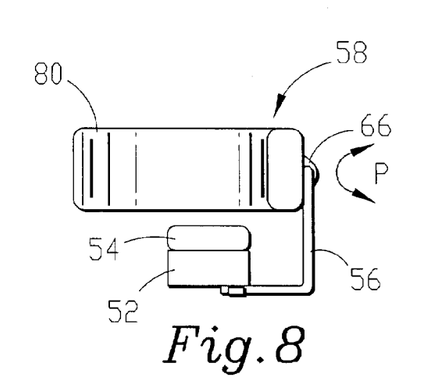
FIG. 8 is a side elevation view of the embodiment of FIG. 7.

Referring now to FIGS. 7 and 8 an alternate embodiment of extension 50 is shown which provides support to an examiner 90 when it is necessary to reach around a large or stout patient who is in a decubitus position on examination table 10 such that the patient's chest wall is situated over access site 40 while the examiner is situated in access site 42 as is generally shown in FIG. 9. Referring to FIG. 9 it will be appreciated that when examiner 90 is conducting an examination of a patient 100 and reaching around the chest and body of patient 100 to apply probe 96 to the chest wall of the patient that depending on the size of patient 100 and the length of the arm of examiner 90 it maybe necessary for examiner 90 to lean across and onto patient 100 to properly apply probe 96 to the chest wall. As can be appreciated, some patients will find this close contact with examiner 90 uncomfortable as may an examiner. In addition, the application of an examiner's weight to an infirm or elderly patient can be problematic and painful to the patient. Therefore, the present invention provides a back support 58 (FIG. 7) which curves around the right side of examiner 90 when seated as shown in FIG. 9. This support allows examiner 90 to lean on an arm portion 80 of back support 58 to thereby support the examiner's weight on arm portion 80 when it is necessary for an examiner 90 (FIG. 9) to reach around a large chested or stout patient 100. It will also be appreciated that additional support for the arm of an examiner 90 could be attached to arm portion 80 by providing an extension support that extends from arm portion 80 toward access site 40 on which the examiner could rest their upper arm while examining a patient. The embodiment of extension 50 shown in FIGS. 7 and 8 has a frame 52 and cushion 54 which are constructed similar to the embodiment of extension 50 shown in FIGS. 4 and 5. The embodiment of extension 50 shown in FIGS. 7 and 8 can be attached to frame 12 of table 10 in the same hinged manner as has been described for the embodiment of FIGS. 4 and 5. It will be appreciated that if an upwardly swinging hinge 60 is utilized a back support having arm portion 80 thereon will need to be withdrawn from post holder 70 attached to frame 52 to allow cushion 54 and frame 52 to be positioned on top of deck 14 of table 10 as previously described for the embodiment of FIGS. 4 and 5.

Referring now to FIGS. 2 and 3 the utility of extension 50 will be further described. First referring to FIG. 3, an examiner is shown positioned in a seated fashion in deck 14 of an examination table 10. When an examiner 90 is so seated within access site 42 only a portion of side 30 of deck 14 is underneath examiner 90 as is shown in FIG. 3 in phantom lines. This precarious positioning of an examiner on deck 14 can result in repetitive strain or stress injuries and back injuries in particular to an examiner due to the lack of support for an examiner's back and the inability of an examiner to position their entire body over deck 14. The present invention as shown in FIG. 2, when attached to the examination table 10 provides added seating width to deck 14 of table 10 and allows an examiner to sit squarely within access site 42 while having the entire body supported on the combination of deck 14 and extension 50. As can now be better appreciated by observing the position of the examiner in both FIGS. 2 and 9 the provision of back support 58 having arm portion 80 allows a right handed examiner position within access site 42 to lean across a large or stout patient 100 (FIG. 9). This is accomplished while maintaining a separation between the body examiner 90 and the body of patient 100 by using arm portion 80 of back support 58 to support examiner 90 and to bear the weight of examiner 90 when it is necessary to lean across a large chested or stout patient 100. In this manner the weight of the examiner is not placed on patient 100 and proper support is provided for the examiner so the examiner's torso and shoulders are not cantilevered out across patient 100 thus presenting substantial stress and potential for injury to the examiner's back.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Certain changes may be made in embodying the above invention, and in the construction thereof, without departing from the spirit and scope of the invention. It is intended that all matter contained in the above description and shown in the accompanying drawings shall be interpreted as illustrative and not meant in a limiting sense.

Having now described the features, discoveries and principles of the invention, the manner in which the inventive sonographer's extension is constructed and used, the characteristics of the construction, and advantageous, new and useful results obtained, the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

Having thus described the invention what is claimed as new and desired to be secured by Letters Patent is as follows:

1. A method of supporting a sonographer on a diagnostic patient support bed while examining a patient, the method comprising:
   providing a patient examination support bed, said bed having a said first access site configured and positioned for receiving a medical examination probe therethrough to contact the heart region of a patient lying on said deck with the patient's head adjacent said first end, and said bed having a second access site configured and positioned for receiving a body portion of an examiner to enable the examiner to reach over a patient and place the probe held in the examiner's hand into contact with the patient's heart region through said first side, and
   attaching a seat to said bed proximate to said second access site in co-planar arrangement with the table deck to extend the plane of said deck outwardly from said access site said attaching providing sufficient support for said outwardly extending seat from said access site to permit the support of at least a portion of the body of a sonographer thereon.

2. The method as claimed in claim 1 further comprising the step of attaching a back support.

3. The method as claimed in claim 1 further comprising the step of attaching a back and arm support.

4. A support for use with an examination table having a deck thereon, said support comprising:
   a seat for connection to an examination table adjacent to an access site, formed in the deck to receive the legs of an examiner therein,
   a hinge to support said seat, said hinge providing movement of said seat between a first and a second position, said first position presenting said seat in co-planar arrangement with the table deck and extending the plane of said deck outwardly from said access site to support the body of an examiner thereon.

5. The support as claimed in claim 4 further comprising a back support portion.

6. The support as claimed in claim 5 wherein said back support portion is connected to said table or said seat.

7. The support as claimed in claim 5 wherein said back support extends to a position between the examiner and the patient.

8. The support as claimed in claim 4 wherein said hinge removably associates said seat with said table.

9. The support as claimed in claim 4 wherein said hinge provides upward movement of said seat into a position above said table deck.

10. The support as claimed in claim 4 wherein said hinge provides downward movement of said seat into a position below said table deck.

11. A patient examination table apparatus comprising:
    a deck,
    said deck presenting a first end and an opposed second end, and a first side and an opposed second side, and including structure defining a first access site adjacent said first side and a second access site adjacent said second side,
    said first side being configured and positioned for receiving a medical examination probe therethrough from below said deck into contact with the heart region of a patient lying on said deck in a first position with the patient's head adjacent said first end,
    said second site being configured and positioned for receiving a body portion of an examiner to enable the examiner to reach over a patient in said first position and place the probe held in the examiner's right hand into contact with the patient's heart region through said first side, a seat for connection to the table said seat being proximate to said second access site, and a hinge to attach said seat proximate to said second access site in co-planar arrangement with said deck to extend the plane of said deck outwardly from said access site and providing movement of said seat between a first position and a second position, said first position presenting said seat in co-planar arrangement with said deck and extending the plane of said deck outwardly from said access site to support the body of an examiner thereon.

12. The table as claimed in claim 11 wherein said means for connection removably associates said seat with the table.

13. The support as claimed in claim 11 further comprising a back support portion.

14. The table as claimed in claim 13 wherein said back support is removably connected to said table or said seat.

15. The table as claimed in claim 13 wherein said back support extends to a position between an examiner and the patient.

16. The table as claimed in claim 11 wherein said hinge provides upward movement of said seat into a position above said deck.

17. The table as claimed in claim 11 wherein said hinge provides downward movement of said seat into a position below said deck.

18. A support for use with an examination table having a deck thereon, said support comprising;
a seat for connection to an examination table proximate to an access site, said access site being formed in the deck to receive the legs of an examiner therein,
a hinge to attach said seat to said table adjacent said access site, said hinge providing movement of said seat between a first and a second position, said first position presenting said seat in co-planar arrangement with the table deck and extending the plane of said deck outwardly from said access site to support the body of an examiner thereon.

19. A support for use with an examination table having a deck thereon, said support comprising:
a seat for connection to an examination table proximate to an access site, said access site being formed in the deck to receive the legs of an examiner therein,
a hinge to attach said seat to said table adjacent said access site, said hinge providing movement of said seat between a first and a second position, said first position presenting said seat in co-planar arrangement with the table deck and extending the plane of said deck outwardly from said access site to support the body of an examiner thereon and said hinge providing upward movement of said seat into a second position above said table deck.

20. A support for use with an examination table having a deck thereon, said support comprising:
a seat for connection to an examination table proximate to an access site, said access site being formed in the deck to receive the legs of an examiner therein,
a hinge to attach said seat to said table adjacent amid access site, said hinge providing movement of said seat between a first and a second position, said first position presenting said seat in co-planar arrangement with the table deck and extending the plane of said deck outwardly from said access site to support the body of an examiner thereon and said hinge providing downward movement of said seat into a second position below said table deck.

21. A patient examination table apparatus comprising:
a deck, said deck presenting a first end and an opposed second end, and a first side and an opposed second side, and including structure defining a first access site adjacent said first side and a second access site adjacent said second side,
said first side being configured and positioned for receiving a medical examination probe therethrough from below said deck into contact with the heart region of a patient lying on said deck in a first position with the patient's head adjacent said first end,
said second site being configured and positioned for receiving a body portion of an examiner to enable the examiner to reach over a patient in said first position and place the probe held in the examiner's right hand into contact with the patient's heart region through said first side,
a seat for connection to the table said seat being proximate to said second access site to extend the plane of said deck outwardly from said access site, and
a hinge to attach said seat proximate to said second access site in co-planar arrangement with said deck to extend the plane of said deck outwardly from said access site, said hinge providing movement of said seat between a first position and a second position, said first position presenting said seat in said co-planar arrangement to support the body of an examiner thereon.

22. A patient examination table apparatus comprising:
a deck, said deck presenting a first end and an opposed second end, and a first side and an opposed second side, and including structure defining a first access site adjacent said first side and a second access site adjacent said second side,
said first side being configured and positioned for receiving a medical examination probe therethrough from below said deck into contact with the heart region of a patient lying on said deck in a first position with the patient's head adjacent said first end,
said second site being configured and positioned for receiving a body portion of an examiner to enable the examiner to reach over a patient in said first position and place the probe held in the examiner's right hand into contact with the patient's heart region through said first side,
a seat for connection to the table said seat being proximate to said second access site to extend the plane of said deck outwardly from said access site, and
a hinge to attach said seat proximate to said second access site in co-planar arrangement with said deck to extend the plane of said deck outwardly from said access site, said hinge providing movement of said seat between a first position and a second position, said first position presenting said seat in said co-planar arrangement to support the body of an examiner thereon and said hinge providing upward movement of said seat into a second position above said table deck.

23. A patient examination table apparatus comprising:
a deck, said deck presenting a first end and an opposed second end, and a first side and an opposed second side, and including structure defining a first access site adjacent said first side and a second access site adjacent said second side,
said first side being configured and positioned for receiving a medical examination probe therethrough from below said deck into contact with the heart region of a patient lying on said deck in a first position with the patient's head adjacent said first end, said second site being configured and positioned for receiving a body portion of an examiner to enable the examiner to reach over a patient in said first position and place the probe held in the examiners right hand into contact with the patient's heart region through said first side, a seat for connection to the table said seat being proximate to said second access site to extend the plane of said deck outwardly from said access site, and a hinge to attach said seat proximate to said second access site in co-planar arrangement with said deck to extend the plane of said deck outwardly from said access site, said hinge providing movement of said seat between a first position and a second position, said first position presenting said seat in said co-planar arrangement to support the body of an examiner thereon and said hinge providing downward movement of said seat into a second position below said table deck.

* * * * *

UNITED STATES PATENT AND TRADEMARK OFFICE
CERTIFICATE OF CORRECTION

| | |
|---|---|
| PATENT NO. | : 7,032,263 B2 |
| APPLICATION NO. | : 10/378,309 |
| DATED | : April 25, 2006 |
| INVENTOR(S) | : Falbo, Michael G., Sr. et al. |

It is certified that error appears in the above-identified patent and that said Letters Patent is hereby corrected as shown below:

Column 11, line 62, replace the word --amid-- after the word adjacent with the word --said--.

Signed and Sealed this

Fourth Day of July, 2006

JON W. DUDAS
*Director of the United States Patent and Trademark Office*